United States Patent [19]

Gregorio et al.

[11] Patent Number: 5,011,979
[45] Date of Patent: Apr. 30, 1991

[54] PROCESS FOR PREPARING METHACRYLATES OF FLUORINATED ALCOHOLS

[75] Inventors: Guglielmo Gregorio; Lamberto Roberti, both of Milan; Ezio Strepparola, Bergamo, all of Italy

[73] Assignee: Ausimont S.R.L., Milan, Italy

[21] Appl. No.: 513,219

[22] Filed: Apr. 23, 1990

[30] Foreign Application Priority Data

Apr. 24, 1989 [IT] Italy ............................. 20269 A/89

[51] Int. Cl.$^5$ ............................................. C07C 69/52
[52] U.S. Cl. .................................................. 560/223
[58] Field of Search ........................................ 560/223

[56] References Cited

U.S. PATENT DOCUMENTS 3,177,185  4/1965  Hollander et al. ............... 560/223
3,766,251 10/1973  Caporiccio ........................ 560/223

FOREIGN PATENT DOCUMENTS 206899 12/1986 European Pat. Off. .

*Primary Examiner*—Paul J. Killos
*Attorney, Agent, or Firm*—Morgan & Finnegan

[57] ABSTRACT

The invention relates to a process for preparing methacrylates of fluorinated alcohols, which consists in reacting said alcohols with an excess of methacrylic acid in the presence of phosphoric anhydride, which acts as a catalyst and absorbs the water which has formed. The process is applicable to primary, secondary and tertiary fluorinated alcohols and to alcohols and diols with perfluoroethereal chains.

11 Claims, No Drawings

PROCESS FOR PREPARING METHACRYLATES OF FLUORINATED ALCOHOLS

DESCRIPTION OF THE INVENTION

The object of the invention is a method for preparing methacrylates of fluorinated alcohols by direct esterification of said alcohols with methacrylic acid.

The methacrylates of fluorinated alcohols exhibiting a high purity degree are particularly suitable for the production of polymers or copolymers with methacrylates of non-fluorinated alcohols, for example methyl methacrylate. These highly transparent polymeric products have a lower refraction index than the polymethyl methacrylate itself, as it is required for particular applications such as for example the coating of optic fibres.

In consideration of the high cost of the fluorinated alcohols it is essential to have available a method for the preparation of methacrylates which does not require an alcohol excess and which, besides providing high yields, permits in the first place to obtain an easily purifiable ester.

Several esterification methods are described in literature, which, however, if applicated to the synthesis of methacrylates of fluorinated alcohols, prove to be little suited to the purpose both because the yields are very low and because the recovery of the products and of the unreacted alcohols involves difficult operations.

J. Hollander and C. Woolf are the first who have synthesized hexafluoroisopropyl methacrylate by reacting hexafluoroisopropanol with methacryloyl chloride in the presence of pyridin, as is described in U.S. Pat. No. 3,177,185 filed on Oct. 28, 1963, with very low yields, about 20% with respect to the alcohol utilized.

M. Kojima et al. (Iyo Kizai Kenkyusho Hokoku, 1983, 17, 37–43; see C.A. 101, 116698 s) have synthesized, in their turn, trifluoroethyl methacrylate and hexafluoroisopropyl methacrylate by reacting methacryloyl chloride respectively with trifluoroethyl alcohol and hexafluoroisopropyl alcohol in the presence of triethylamine, with quite unsatisfactory yields of 14–15%.

The direct esterification, i.e. the reaction between acid and alcohol, according to the art, seemed not suited to alcohols having an acid nature, as are the fluorinated alcohols. In fact, the equilibrium of the type:

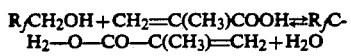

$R_fCH_2OH+CH_2=C(CH_3)COOH \rightleftarrows R_fCH_2-O-CO-C(CH_3)=CH_2+H_2O$ where $R_f$ represents a fluorinated radical, is not shifted towards the formation of the ester.

In the esterification field, in general, the use of a strong dehydrating agent, such as sulphuric acid or phosphoric anhydride, is not free from drawbacks, as these dehydrating agents react with most of the alcohols, thereby giving rise to ethers or olefins. Also many organic acids react with formation of ketenes or anhydrides and the unsaturated acids tend to polymerize.

By consequence, the use of a dehydrating agent cannot be considered as suitable for the preparation of any ester.

In particular, phosphoric anhydride has been used very seldom in the esterification reaction. As it is stated by A. Banerjee et al., J. Org. Chem. 1983, 48, 3106–08, the only example of use of phosphoric anhydride in such reaction, before these Authors, is reported in the article by J. M. Church and L. Lynn, Ind. Eng. Chem. 1950, 42, 768, which describes the esterification of methacrylic acid with methanol in the presence of phosphoric anhydride, operating with an alcohol/acid molar ratio equal to 2.5.

A. Banerjee et al. describe, in the above-cited article, the preparation of esters starting from various acids and alcohols in the presence of phosphoric anhydride, operating with a considerable alcohol excess. The Authors state that with certain acids the reaction proceeds with high yields, while with other acids the reaction takes place with very low yields or does not take place at all, even if it is operated with a great excess of phosphoric anhydride, what is indicative of the unforeseeable nature of the reaction. Furthermore, according to the Authors, the method is not suited to the esterification of secondary or tertiary alcohols.

Anyhow, no examples of direct esterification of acids with fluorinated alcohols can be found in literature.

The object of the present invention is to provide a process which permits to obtain methacrylates of fluorinated alcohols at a high purity degree, by direct esterification of said alcohols with methacrylic acid, with high yields with respect to the alcohols.

This object is achieved by the process of the present invention, which consists in reacting a fluorinated alcohol with a methacrylic acid excess, in the presence of phosphoric anhydride, at a temperature ranging from 30° to 150° C., preferably from 80° to 105° C.

The molar ratio between methacrylic acid and hydroxyl groups of the alcohol ranges from 1 to 10, preferably from 2 to 5.

The utilized phosphoric anhydride must be in the activated form, i.e. in a finely crystalline form. The phosphoric anhydride/hydroxyl groups molar ratio ranges from 0.2 to 5.

The esterification method forming the object of the present invention is applicable to primary, secondary and tertiary alcohols having general formula:

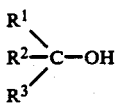

wherein $R^1$, $R^2$ and $R^3$, same or different, represent a perfluoroalkyl radical, an aromatic non-fluorinated hydrocarbon radical or hydrogen, and wherein one of $R^1$, $R^2$ and $R^3$ is a perfluoroalkyl radical.

Preferably $R^1$, $R^2$ and $R^3$, same or different, are $C_1$-$C_4$ perfluoroalkyl or phenyl, tolyl, xylyl radicals.

As an example of primary alcohols it is possible to indicate $CF_3CH_2OH$ and higher homologouses; as an example of secondary fluorinated alcohols, $CF_3$—CHOH—$CF_3$ and as an example of tertiary fluorinated alcohols:

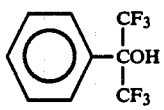

The method is applicable also to primary, secondary and tertiary fluorinated diols and polyols, such as:

The esterification method which is the object of the invention is furthermore applicated to alcohols having a perfluoropolyethereal chain of the type:

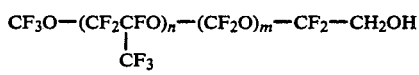

These latter alcohols are generally utilized as mixtures in which n and m are differently distributed integers so as to give rise to average molecular weights ranging from 400 to 2,500, and they are obtained according to the methods described in U.S. Pat. Nos. 3,513,203; 3,847,978; 3,810,174. The method is applied also to diols exhibiting a perfluoropolyethereal chain having two end groups $CH_2OH$ at its ends, of the type $HOCH_2—CF_2O(CF_2CF_2O)_n(CF_2O)_mCF_2CH_2OH$ such as those obtainable by the method described in U.S. Pat. No. 3,810,874, and with n and m being such integers as to give rise to mixtures having an average molecular weight from 500 to 5,000.

The recovery of the product from the reacting mixture is relatively simple. In the cases of methacrylates of alcohols such as trifluoroethanol or hexafluoroisopropanol and, at any rate, of products having—a remarkably lower boiling point than the one of methacrylic acid, after separation of phosphoric acid and of residual phosphoric anhydride by decantation, distillation is carried out directly.

In the case of high-boiling fluorinated alcohols, methacrylic acid, phosphoric acid and residual phosphoric anhydride are separated by washing with water or with water and sodium bicarbonate or, particularly for the high molecular weight alcohols which are insoluble in the common organic solvents, methacrylic acid and the other foreign matters are removed by washing with acetone.

If particular measures are taken, a few of the high-boiling esters can be distilled under vacuum.

The phosphoric anhydride utilized in these preparations shall be in the activated form, i.e. in the form of a finely crystalline powder.

Furthermore, it is preferably operated in the presence of polymerization inhibitors, such as di-tert.butyl-p-cresol, tert.butyl-catechol, p-methoxyphenol etc.

As already mentioned, the obtained products easily reach the purity degree required for the polymerizations. For example, the methyl methacrylate and hexafluoroisopropyl methacrylate mixture containing from 10% to 40% of hexafluoroisopropyl methacrylate, prepared in this manner and directly distilled from the rought product, can be polymerized, thereby obtaining a high molecular weight copolymer which does not give rise to phase segregation and therefore appears homogeneous and transparent.

The same occurs with the trifluoroethanolmethacrylate prepared by the present method.

The method of the present invention is specific for the esterification of methacrylic acid with fluorinated alcohols and cannot be applied to the esterification of other unsaturated acids. In fact, in the case of other unsaturated acids, for example acrylic acid, the ester yields are low and oligomers of the same acid are formed.

The following examples are given for illustrative purposes, but they are not to be considered as a limitation of the present invention.

EXAMPLE 1

416 g of methacrylic acid, 3 g of di-tert.butyl-p-cresol, as polymerization inhibitor, and 101 g of phosphoric anhydride were poured into a one-liter flask equipped with mechanical stirrer, thermometer, heating and cooling system. The whole was stirred and 270 g of hexafluoroisopropanol were added. It was heated to 100° C. for 75 minutes. It was cooled and the phases were separated. From the methacrylic phase, by vacuum distillation, 328.4 g of pure hexafluoroisopropanol methacrylate (b.p. 47° C. at 100 mm Hg) were recovered, the yield being of 86.4% calculated on the fluorinated alcohol.

EXAMPLE 2

155 g of methacrylic acid, 1.5 g of ter.-butyl-p-cresol and 38 g of phosphoric anhydride were poured into a 250 ml flask equipped with mechanical stirrer, thermometer, heating and cooling system. It was stirred and 60 g of trifluoroethanol were added. It was heated to 60° C. for 60 minutes. It was cooled and the phases were separated. From the methacrylic phase, by distillation under vacuum, 84.8 g of pure trifluoroethanol methacrylate (b.p. 40° C. at 50 mm Hg) were recovered. The yield was equal to 84%.

EXAMPLE 3 (comparative test)

44 g of acrylic acid, 1.5 g of di-tert.butyl-p-cresol and 13.8 g of phosphoric anhydride were poured into a 250 ml flask equipped with mechanical stirrer, thermometer, cooling and heating system. It was stirred and 33.5 g of hexafluoroisopropanol were added. It was heated to 100° C. After 60 minutes, all the acrylic acid was consumed, while 30% of hexafluoroisopropyl alcohol had remained unconverted. Furthermore, several high-boiling products were present. The GCC/SM analysis revealed that they were acrylic acid oligomers, a part of which was esterified with hexafluoroisopropanol.

From the foregoing it is apparent that the method of the present invention is specific for methacrylic acid and cannot be applicated to other unsaturated acids.

EXAMPLE 4

A mixture of alcohols having perfluoropolyethereal chain of general formula:

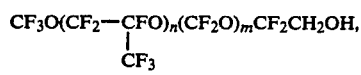

and an average molecular weight of 600, was subjected to esterification with methacrylic acid. 70 g of this mixture (0.117 moles of alcohol) were treated with 50 g (0.58 moles) of methacrylic acid, 8.5 g (0.06 moles) of phosphoric anhydride and 0.5 g of tert.butyl catechol as a polymerization inhibitor.

It was heated to 100° C. under stirring for 1 hour. After cooling, it was washed with water, thereby separating the phases; then it was repeatedly washed with an aqueous solution of sodium bicarbonate.

The remaining organic product consisted of 69.5 g of methacrylic esters of the fed alcohols. The liquid, just slightly colored and rendered limpid by filtration, exhibited an I.R. infrared spectrum in which the bands due to alcohol and to methacrylic acid were missing. An intense band at 1745 cm$^{-1}$ due to the ester was present.

EXAMPLE 5

A mixture of difunctional alcohols with perfluoropolyethereal chain terminating with two methyl alcoholic groups of general formula:

$$HOCH_2CF_2O(CF_2CF_2O)_m(CF_2O)_nCF_2CH_2OH$$

having an average molecular weight equal to 4,000, prepared as is described in U.S. Pat. No. 3,810,874, was utilized for the esterification with methacrylic acid.

200 g of the diol mixture were added to 65 g (0.75 moles) of methacrylic acid, 1.5 g of p.methoxyphenol as a polymerization inhibitor and 8 g of phosphoric anhydride.

It was heated to 80° C. for 20 hours under intense stirring, checking from time to time the conversion degree on a sample by means of I.R. infrared spectrometry and $^{19}$F-N.M.R.

After 20 hours, the N.M.R. signals of the starting alcohol compound were strongly reduced, while the I.R. band at 1745 cm$^{-1}$ due to the esters was intense. In order to obtain an absolutely pure product it is advisable to add further 8 g of phosphoric anhydride to the mixture and to go on heating for further 10 hours.

After cooling and decantation, the product was repeatedly washed with acetone (in which it is insoluble) in order to remove the methacrylic acid excess, whereafter it was dried under vacuum. Now, N.M.R. signals due to the CF$_2$CH$_2$OH were no longer detectable and the ester number was corresponding to the equivalent weight of the diol.

The product can be further purified by washing with ethyl ether.

What is claimed is:

1. A process for preparing methacrylate of fluorinated alcohols, comprising the fluorinated alcohol is reacted with a methacrylic acid excess in the presence of a phosphoric anhydride excess, at a temperature ranging from 30° to 150° C.

2. The process according to claim 1, wherein the fluorinated alcohol is a primary, secondary or tertiary alcohol of formula:

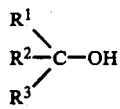

wherein R$^1$, R$^2$ and R$^3$ same or different, represent a perfluoroalkyl radical, a non-fluorinated aromatic hydrocarbon radical or hydrogen and in which at least one of R$^1$, R$^2$ and R$^3$ is a perfluoroalkyl radical.

3. The process according to claim 2, wherein R$^1$, R$^2$ and R$^3$, same or different, are C$_1$-C$_4$-perfluoroalkyl or phenyl, tolyl, xylyl radicals.

4. The process according to claim 2, wherein the fluorinated alcohol is trifluoroethanol.

5. The process according to claim 2, wherein the fluorinated alcohol is hexafluoroisopropanol.

6. The process according to claim 2, wherein the fluorinated alcohol is a mixture of alcohols with perfluoropolyethereal chain of formula:

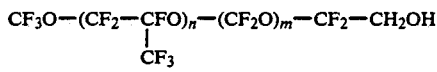

in which n and m are integers such that the average molecular weight ranges from 400 to 2,500.

7. The process according to claim 1, wherein the fluorinated alcohol is a diol or a polyol.

8. The process according to claim 6, wherein the fluorinated alcohol is a mixture of diols of formula:

$$HOCH_2-CF_2O(CF_2-CF_2O)_n(CF_2O)_m-CF_2-CH_2OH$$

in which n and m are integers such that the average molecular weight ranges from 500 to 5,000.

9. The process according to claim 1, wherein the molar ratio between methacrylic acid and OH groups of the alcohol ranges from 1 to 10.

10. The process according to claim 1, wherein the molar ratio between phosphoric anhydride and OH groups of the alcohol ranges from 0.2 to 5.

11. The process according to claim 1, wherein the temperature range is from 80° to 105° C.

* * * * *